May 2, 1967 D. H. MOREY, JR Plant Pat. 2,736
ROSE PLANT
Filed April 22, 1966
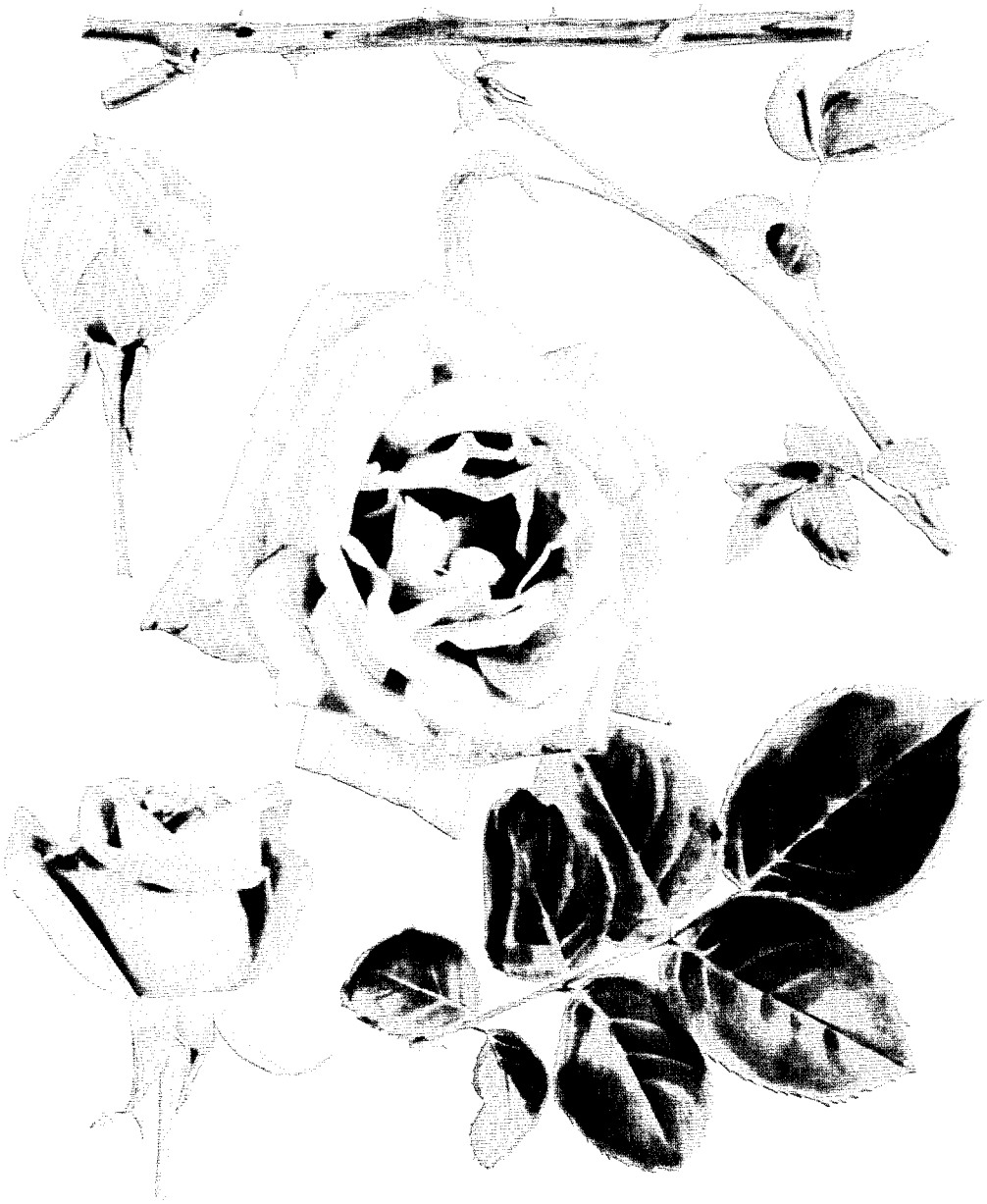
Inventor.
Dennison H. Morey, Jr.
By: Robb & Robb
Attorneys.

United States Patent Office

Plant Pat. 2,736
Patented May 2, 1967

2,736
ROSE PLANT

Dennison H. Morey, Jr., Santa Rosa, Calif., assignor to Jackson & Perkins Company, Newark, N.Y., a corporation of New York

Filed Apr. 22, 1966, Ser. No. 544,635
1 Claim. (Cl. Plt.—20)

The present invention relates to a new and distinct variety of rose plant of the hybrid tea class, which was originated by me crossing an annamed and unpatented red flowered seedling of unidentified parentage with the variety known as "Talisman" (unpatented).

The primary objective of this breeding was to produce a new hybrid tea rose variety which has a bushy and free blooming habit and which bears flowers of a brilliant color. This objective was fully achieved, along with other desirable features, as evidenced by the following unique combination of characteristics which are outstanding in the new variety and which distinguish it from its parents, as well as from all other varieties of which I am aware:

(1) A vigorous, upright and bushy habit of growth;
(2) Foliage of the "Talisman" type;
(3) Free flower production;
(4) A distinctive, attractive and unusually brilliant red flower color corresponding to Spectrum Red, very lightly overcast with Scarlet-Red; and
(5) A strong "Old Rose" flower fragrance.

Asexual reproduction of my new variety by budding, as performed at Pleasanton, Calif., and also at Newark, N.Y., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed red flowered seedling of unidentified parentage.
*Pollen parent.*—"Talisman."
Classification:
*Botanic.*—Hybrid tea.
*Commercial.*—Hybrid tea.

*Flower*

(Observations made from specimens grown outdoors at Newark, N.Y., in the early morning during the latter part of the month of August.)

Blooming habit: Recurrent—continuous; free production of flowers.
Bud:
*Size.*—Large.
*Form.*—From ovoid to urn-shaped; it is not affected by wet or hot weather.
*Color.*—When sepals first divide—Oxblood Red, Plate 1. When petals begin to unfurl—Carmine Red, Plate 1, very lightly overcast with Spectrum Red, Plate 1. When half-blown:—inside of petals—Nopal Red, Plate 1, very lightly overcast with Spectrum Red, Plate 1; reverse of petals—Spectrum Red, Plate 1, lightly overcast with Nopal Red, Plate 1.
*Sepals.*—Slightly branched; curl back when petals begin to unfurl. Color: inside—Base Turtle Green, Plate 32, with upper part of sepal Biscay Green, Plate 17; outside—Oil Green, Plate 5.

*Calyx.*—Color—Oil Green, Plate 5. Shape—funnel. Size—long. Aspect—smooth. Odor when rubbed—none.
*Peduncle.* — Length — medium. Aspect — smooth. Strength—erect; heavy. Color—Courge Green, Plate 17.
*Opening.*—Opens up well; is not affected by adverse weather conditions.
Bloom:
*Size.*—Large. Average size when fully expanded—from 5 inches to 5½ inches.
*Borne.*—Singly.
*Stems.*—Medium length; strong.
*Form (when first open).*—Cupped. Permanence—retains its form to the end, but outer petals curl back slightly.
*Petalage.*—Double (full but open center). Number of petals under normal conditions—from 25 to 30.
*Color.*—Center of flowers—Scarlet Red, Plate 1, lightly overcast with Spectrum Red, Plate 1. Outer petals—Nopal Red, Plate 1, lightly overcast with Spectrum Red, Plate 1. Base of Petals (aiglet)—Apricot Yellow, Plate 4. Inside of petals—Spectrum Red, Plate 1, very lightly overcast with Scarlet-Red, Plate 1. Reverse of petals—Spectrum Red, Plate 1, very lightly overcast with Nopal Red, Plate 1. General tonality from a distance—Scarlet-Red, Plate 1.
*Discoloration.*—General tonality at end of first day—Scarlet-Red, Plate, overcast with Spectrum Red, Plate 1. Second day—Scarlet-Red, Plate 1, lightly overcast with Spectrum Red, Plate 1. Third day—Scarlet-Red, Plate 1.
Petals:
*Texture.* — Thick; is not affected by wet or hot weather.
*Appearance.*—Inside—velvety. Outside—satiny.
*Form.*—Oval; slightly notched.
*Arrangement.* — Imbricated (regularly arranged shingle-like).
*Petaloids in center.*—Few; large.
*Persistence.*—Drop off cleanly.
*Fragrance.*—Strong. Nature—"Old Rose perfume" (centifolia).
*Lasting quality.*—On the plant—long. As cut flower—long.

*Genital organs*

Stamens, anthers: Medium size, many; regularly arranged around styles. Color—Deep Chrome, Plate 3.
Stamens, filaments (threads): Medium length. Color—Scarlet-Red, Plate 1.
Pollen: Color—Pale Orange-Yellow, Plate 3.
Styles: Bunched; uneven length; medium length; thin.
Stigmas: Color—Ivory Yellow, Plate 30.
Ovaries: All enclosed in calyx.
Hips: None.
Seeds: None.

*Plant*

Form: Bush.
Growth: Vigorous; upright.
Foliage: Compound of 3–7 leaflets.
*Size.*—Medium.
*Quantity.*—Normal.
*Color.*—New foliage: upper side—Vinaceous-Rufous, Plate 14, with center of leaf lightly overcast with Citrine, Plate 4; under side—Eugenia Red, Plate 13. Old foliage: upper side—Deep Dull Yellow Green (1), Plate 32; under side—Light Bice Green, Plate 17.

*Shape.*—Oval.

*Texture.* — Upper side — leathery; glossy. Under side—smooth.

*Ribs and veins.*—Ordinary.

*Edge.*—Serrated (saw toothed).

*Serration.*—Both double and single; small.

*Leaf stem.*—Color—Russet, Plate 15. Under side—smooth.

*Stipules.*—Medium length; smooth.

Wood:

*New wood.*—Color—Mignonette Green, Plate 31, very lightly overcast with Corinthian Red, Plate 27. Bark—smooth.

*Old wood.*—Color—Cress Green, Plate 31. Bark—smooth.

Thorns:

*Thorns.* — Quantity: on main stalks from base — ordinary; on laterals from stalk — ordinary. Form — narrow base; medium length; hooked downward. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous, upright and bushy habit of growth, foliage of the "Talisman" type, free flower production, a distinctive, attractive and unusually brilliant red flower color corresponding to Spectrum Red, very lightly overcast with Scarlet-Red, and a strong "Old Rose" flower fragrance.

No references cited.

ANTONIO F. GUIDA, *Acting Primary Examiner.*

ROBERT E. BAGWILL, ABRAHAM G. STONE, *Examiners.*